US008015975B2

(12) United States Patent
Zohlmann, Jr.

(10) Patent No.: US 8,015,975 B2
(45) Date of Patent: Sep. 13, 2011

(54) SPOUSAL POSITIONAL DEPENDENT SNORING AND POSITIONAL DEPENDENT SLEEP APNEA GARMENT

(75) Inventor: William Thomas Zohlmann, Jr., Palm Coast, FL (US)

(73) Assignee: Family Concepts TJH, LLC, Salt Lake City, UT (US)

( * ) Notice: Subject to any disclaimer, the term of this patent is extended or adjusted under 35 U.S.C. 154(b) by 0 days.

(21) Appl. No.: 11/495,497

(22) Filed: Jul. 28, 2006

(65) Prior Publication Data

US 2008/0023011 A1    Jan. 31, 2008

(51) Int. Cl.
*A61F 5/56* (2006.01)
(52) U.S. Cl. ........................................ 128/848
(58) Field of Classification Search ................ 128/848, 128/846; 2/115, 125, 127, 133
See application file for complete search history.

(56) References Cited

U.S. PATENT DOCUMENTS

| | | | |
|---|---|---|---|
| 2,304,235 A * | 12/1942 | Boots | 2/1 |
| 2,562,725 A | 7/1951 | Leto et al. | |
| 2,629,884 A | 2/1953 | McMonagle | |
| 2,765,480 A | 10/1956 | Mueller | |
| 2,952,856 A | 9/1960 | Ruff | |
| 3,485,241 A * | 12/1969 | Polley | 128/871 |
| 3,924,282 A | 12/1975 | Bond | |
| 4,274,673 A | 6/1981 | Kifferstein | |
| 4,506,396 A | 3/1985 | Ritchie et al. | |
| 4,528,981 A | 7/1985 | Behar | |
| 4,744,117 A | 5/1988 | Bond | |
| 5,040,546 A | 8/1991 | Deluhery | |
| 5,044,026 A | 9/1991 | Matthews | |
| 5,165,130 A | 11/1992 | Wendling | |
| 5,182,828 A | 2/1993 | Alivizatos | |
| 5,189,748 A | 3/1993 | Garrusin et al. | |
| 5,193,238 A | 3/1993 | Clute | |
| 5,216,772 A | 6/1993 | Clute | |
| 5,272,780 A | 12/1993 | Clute | |
| 5,289,748 A | 3/1994 | Kuchta et al. | |
| 5,310,245 A | 5/1994 | Lyszczasz | |

(Continued)

OTHER PUBLICATIONS

Rematee Positional Sleeping Solutions for Sleep Apnea, Maternity, Snoring; 2009; 4 pages.

(Continued)

*Primary Examiner* — Patricia Bianco
*Assistant Examiner* — Tarla Patel
(74) *Attorney, Agent, or Firm* — Thorpe North & Western LLP

(57) ABSTRACT

A garment designed to discourage supine sleep which intensifies snoring and apnea levels in some people. Obstructive Sleep Apnea and Snoring occur when the tongue and throat muscles relax during sleep. At that point they fall back and block the airways causing the apneas and worsening snoring. A significant percentage of snoring and OSA is position related and symptoms worsen by sleeping in a supine position. Garment or other embodiments have a (partial) less than ½ of the circumference mounted pouch which allows the insert to self center and pivot on the spine and have movement between shoulders as the user is sleeping and attempts to move towards the back from his or her side. The placement at lower neck area presses slightly against the spine to influence head to tilt up and slightly close mouth while sleeping thereby increasing the airway opening. The insert while comfortable to sleep against is of enough diameter or depth and made of a cushion type of material to discourage supine and encourage side sleeping without any discomfort to user. The garment or other embodiments have frontal body fasteners for ease of putting on and taking off.

8 Claims, 4 Drawing Sheets

U.S. PATENT DOCUMENTS

| | | |
|---|---|---|
| 5,341,531 A | 8/1994 | Straub et al. |
| 5,347,669 A | 9/1994 | Neviaser et al. |
| 5,359,739 A | 11/1994 | Rains et al. |
| 5,367,730 A | 11/1994 | Sher |
| 5,499,418 A | 3/1996 | Tan et al. |
| 5,522,104 A | 6/1996 | Little |
| 5,530,974 A | 7/1996 | Rains et al. |
| 5,535,467 A | 7/1996 | Ciske |
| 5,581,832 A | 12/1996 | Bridley |
| 5,754,998 A | 5/1998 | Selton |
| 5,910,080 A | 6/1999 | Selton |
| 6,009,873 A | 1/2000 | Neviaser |
| 6,067,679 A | 5/2000 | Rice |
| 6,081,950 A | 7/2000 | Selton |
| 6,381,787 B1 | 5/2002 | Rogone et al. |
| 6,560,800 B1 | 5/2003 | Draves |
| 6,640,366 B1 | 11/2003 | Draves |
| 6,698,432 B2 | 3/2004 | Ek |
| 6,877,176 B2 | 4/2005 | Houghteling |
| 6,886,201 B1 | 5/2005 | Weiss-Lohrei |
| 6,954,954 B2 | 10/2005 | Stelnicki |
| 6,971,715 B2 | 12/2005 | Hankins |
| 7,117,553 B2 | 10/2006 | Fairchild et al. |
| 7,134,435 B2 | 11/2006 | Scott |
| 7,360,265 B2 | 4/2008 | Lamer |
| 7,874,032 B2 | 1/2011 | North et al. |
| 2001/0015208 A1* | 8/2001 | Konishi ................. 128/848 |
| 2003/0200590 A1* | 10/2003 | Haskell .................... 2/69 |
| 2004/0031492 A1* | 2/2004 | Kawamura ............. 128/848 |
| 2007/0256695 A1* | 11/2007 | Crocetti ................ 128/848 |
| 2009/0229054 A1 | 9/2009 | Yates et al. |
| 2009/0229618 A1 | 9/2009 | Sotelo et al. |
| 2009/0313760 A1 | 12/2009 | Blake et al. |
| 2010/0088824 A1 | 4/2010 | Tanner |
| 2010/0319131 A1 | 12/2010 | North |

OTHER PUBLICATIONS

U.S. Appl. No. 12/975,144, filed Dec. 21, 2010; Vaughn W. North.

U.S. Appl. No. 12/898,556, filed Oct. 5, 2010; Vaughn W. North.

* cited by examiner

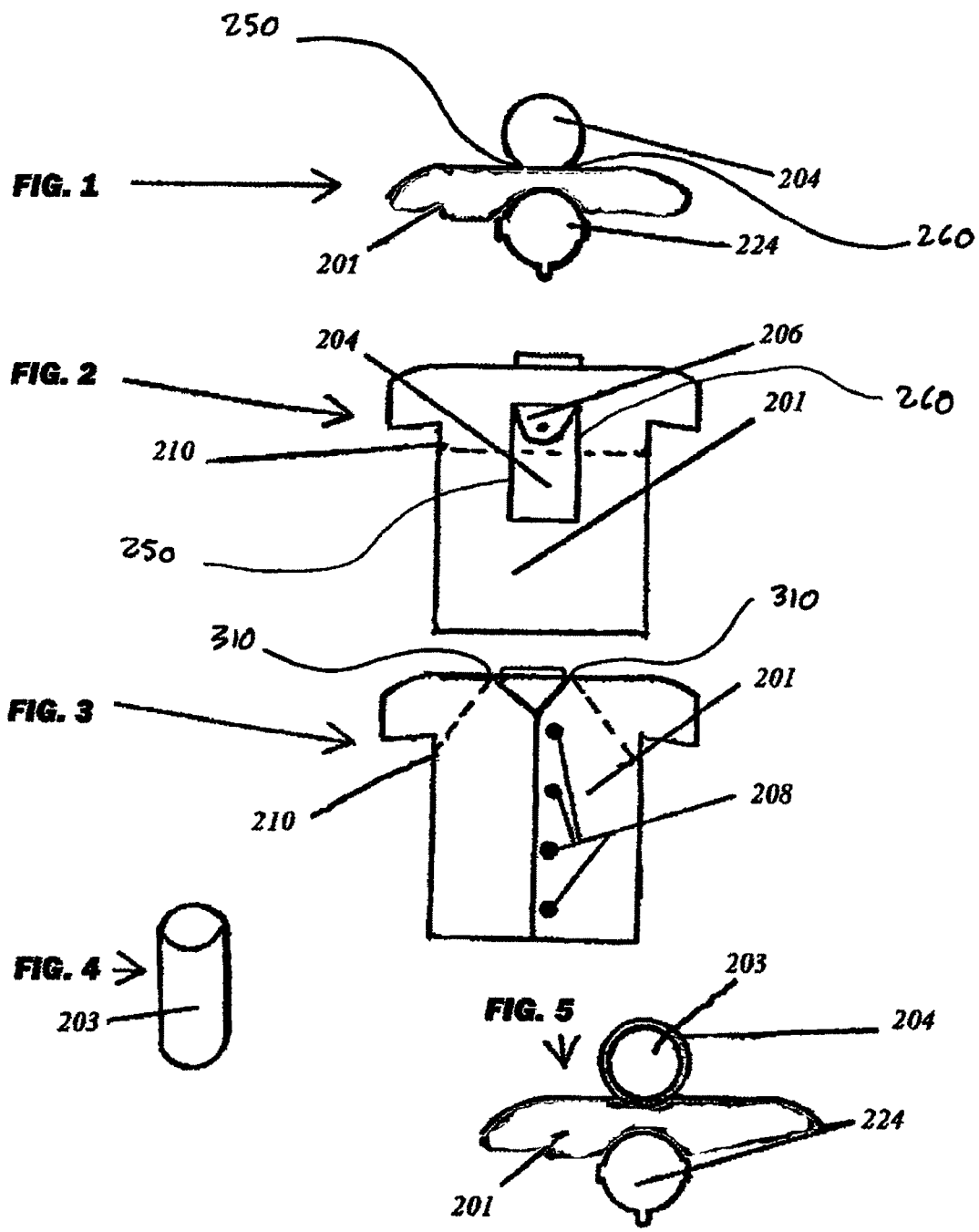

SPOUSAL POSITIONAL DEPENDENT SNORING AND POSITIONAL DEPENDENT SLEEP APNEA GARMENT

BACKGROUND OF THE INVENTION

1. Field of Invention

The invention relates to the field of devices to limit the ability of users who are asleep to roll on to their backs while they are sleeping which create or worsen positional dependent sleep apnea or snoring.

2. Description of Related Art

Sleep centers are instructing patients who can not tolerate continuous positive air pressure equipment to sew tennis balls in a sock to the back of their sleepwear. Reference U.S. Pat. Nos. 2,304,235, Des.398,139, Des.362,331 sleeping garments—which incorporate that principle. This does not inhibit lying in a supine position as the t shirt does not adequately fix the ball on the spine and you have to be in a complete supine position to even feel it. When you do it is uncomfortable and disturbs sleep. Other alternatives suggested are throat surgery that does not always produce desired effects and in most cases is irreversible. Dental appliances which keep mouth mostly closed or position lower jaw forward, head bands that do a similar thing, pillows that help in positioning and some very involved and intricate devices that keep the user in the side sleeping position. Other prior art: Infant sleeping garment (reference U.S. Pat. No. 3,485,241)-Polley—Is not mounted in a similar manner and is not for the medical conditions. Snore reducer jacket—(reference U.S. Pat. No. 6,289,893)-Levitt—does not consistently resist rolling into the supine position and uses a different design. Apnea prevention gear (reference U.S. Pat. No. 6,779,526) Kawamura—has inserts that cause discomfort to force side sleep. Motion limiting device (reference U.S. Pat. No. 6,357,444)-Parker—has to be adjusted and readjusted and uses a different device. Devices with alarms include, Keep off your back alarm (reference U.S. Pat. No. 5,081,447)-Echols—and Sleepwear (reference U.S. Pat. No. 5,036,865)—Keaton, use an alarm which either shocks or makes noise waking up sleeper and nearby other sleeper.

3. Background

Snoring and Obstructive Sleep Apnea are very prevalent and serious conditions. The person who has one of these conditions also interrupts the sleep of their spouse or anyone sleeping near them. Snoring affects over 25% of the population including adults and some children. Of those a significant percent are considered serious snorers. The snoring occurs when the tongue and soft tissue at the rear base of the tongue fall back into the airway and vibrates as a person breathes through the narrowed airway. This affects the amount of air entering the airway. It is usually worsened when someone is sleeping on their back. Serious snorers usually require some sort of prevention, intervention or treatment. The condition usually has a very negative effect on the ability of the nearby other sleeper or sleepers to get restful sleep. It is also a less restful sleep for the snorer which affect their daytime performance. Obstructive Sleep Apnea is a condition where breathing is interrupted and stopped while a person sleeps. It affects approximately 5% of the population including adults and some children. It is a very serious condition. It is caused when the person is in deep sleep and their tongue and upper soft throat tissues fall back and collapsing and or blocking the upper airway. The condition is associated with increasing average blood pressure levels, increasing stroke and other heart condition risks. The prominent symptoms are loud snoring and snorting and stopping of breathing while asleep and excessive sleepiness during the waking hours. The person with the condition usually finds out because the people around them tell them. It also affects the other persons sleep because they know the person with the apneas stopped breathing. The person with the condition is usually unaware of it. The sleep study confirms the condition. The current treatment for controlling snoring and Obstructive Sleep Apnea are concentrated on maintaining an open airway to allow uninterrupted breathing. The most used method practiced is CPAP or Continuous Positive Airway Pressure machine. This involves wearing a nasal or full face (mouth and nose) mask. The OSA patient hooks themselves up to the machine every night when they go to bed and must take it with them if they are staying out overnight. This is the direction the medical community is currently taking. Many users discontinue use after a few months even against their doctors advise. This is one of the main reasons insurance companies initially rent these machines instead of buying them.

Other treatments include throat surgery, dental appliances, pillows, some other type of restraints that require on going adjustments or create noise or pain which make them non user friendly. Also existing positioning devices are uncomfortable and disturb sleeper. It is published by the American Sleep Apnea Association and Chest that a significant number Obstructive Sleep Apnea and Snoring sufferers are position dependent. They have most of their apneas amd loud snoring while sleeping on their backs. Their symptoms disappear or are reduced when they sleep on their sides. A comfortable user friendly positioning device has long been needed and this invention addresses this need for many sufferers.

BRIEF SUMMARY OF THE INVENTION

The garment has a rear pouch mounted in a new innovative and novel approach which allows varied users to wear it without adjusting. Because of the partial circumference mounting of pouch it forms an indentation which makes garment pouch always seek the spinal cavity area of back while permitting a controlled movement of body (for snoring and sleep apnea this range will ideally be between 60 to 90 degrees) which 90 being the side sleep position. Partial circumference mounting is the attachment of the insert cylinder pouch to the rear of a garment in the following manner. The pouch is mounted along the spinal area from shoulder area or below in any length towards lower back. The round cylinder pouch is mounted on garment to allow lateral motion by using a measured portion of the circumference to attach pouch. These mounting points of pouch on garment are less than ½ of the circumference of the pouch and insert and run the length of pouch vertically from shoulders to lower back on both sides of spinal column using it as a centering point. The example used here is to further clarify this by using a 12" length pouch and insert having an 8" diameter. The 8" diameter has a 25" circumference. Of this 25" circumference 1" up to 11.5" (less than ½ of the) circumference is used to attach to garment. The smaller the amount of this attachment the greater the lateral rotation of the pouch between shoulders.

When user is lying on their side in bed and moves it is constantly attempting to remain in the spinal cavity with a controlled movement slightly between shoulders of user. Unlike prior or related devices this allows for the unconscious movement we experience when we are asleep. As the sleeper attempts to roll between his or her back and side the pouch with insert pivots slightly and detents into the cavity and moves slightly towards shoulders and the user comes up against a bolster pillow effect. Because they are asleep their body is relaxed and stays in this position. This also does not disturb or wake them or their partner as other devices do. To the user it feels very comfortable like they are sleeping against a pillow. Also because the users body is constantly attempting to either be on its side or back (with most sleepers), this garment convinces the body to stay in a side position. While user is lying on his or her side in bed it also presses slightly against upper spinal and lower neck area pressing it forward slightly which can help to keep users mouths slightly closed. Because of reduced levels of apneas and snoring they and (or) their sleeping partner also get a more restful sleep. When user gets up from bed during the night the pouch and insert settle into the spinal cavity and user can do most things normally done without removal or adjustment. This type of mounting creates a constant attempt by pouch and insert combination to remain on the spine and allows for a simple one step use of garment. Just put it on like a pajama top or nightshirt and lay on your side in bed. The user can without adjusting lift up a little and roll over and change which side they are sleeping on. The garment has frontal fasteners adjustable or fixed.

Another optional item for some users is an elastic strap mechanism from front of neck opening to below arms that may also extend around back which in some cases creates a better fit for the user of the garment which enhances the performance and feel for some. Another feature is due to the partial circumference mounting of the pouch the width and length of mounting offset can be varied. Also the diameter, depth, width, length and external shape of the insert and pouch can be varied and increased or decreased thereby leading to the ability of the medical community to custom fit the garment to make the sleeping position of user a controlled issue. What this allows is for the professional to put the user in a controlled either side tilt from slight to over 90 degrees. Which enables the over side positioning of some users towards the bed surface for some medical conditions. This is obtainable with a sized to user minimal to no adjusting nightshirt, vest or other garment. Independent Backpack, Pouch, Brace or Girdle may require body and or shoulder strap adjustments.

Pouch circumference size can be adjustable either by exchanging pouches or inserts on garment or by adjustable fasteners on the pouch. Pouch can have varied means of access and fasteners to remove or change insert. Garment is washable. This invention is a reliable, comfortable and easy to use alternative to current treatments.

BRIEF DESCRIPTION OF THE SEVERAL VIEWS OF THE DRAWINGS

FIG. 1 Is the top back view of pouch and shirt without the insert or flap sized for user Extending out from back of shirt and will indent in spinal area when insert is in due to circumference mounting.

FIG. 2 Is the back of shirt with elastic, pouch showing less than ½ circumference mounting, upper spine lower neck placement and securable flap for installing and removing insert.

FIG. 3 Is the front view of the shirt (shown with fasteners and elastic).

FIG. 4 Is insert (sized and may be other shape depending on need of user) foam, airbladder or other material.

FIG. 5 Is top back view of pouch and shirt (without flap) showing that the circular insert (sized and may be other shape depending on need of user) projects into shirt due to indenting (less than ½ of) circumference mounting and out from back of shirt sized to user.

DETAILED DESCRIPTION OF THE INVENTION

Description of the Preferred Embodiments

Figure 6:
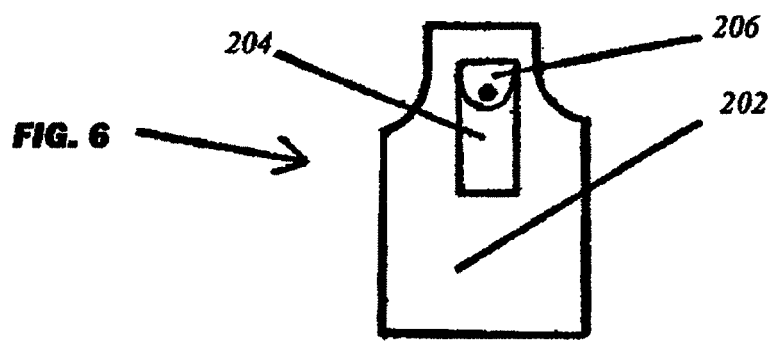
FIG. 6 Is the back of vest with pouch and securable flap for installing and removing insert.

In the following detailed description of the preferred embodiments, reference is made to the accompanying drawings which form a part hereof, and in which are shown by way of illustration specific embodiments in which the invention may be practiced. It is to be stated and understood that other embodiments may be utilized and structural changes may be made without departing from the scope of the present invention.

Referring To

FIG. 1 is cross section view looking down from the top at the pouch 204 (without flap 206) to show the rear of the shirt 201 without the insert 203. The circumference mounting indents into shirt and spinal area of user (when the insert 203 is put into pouch 204). The size of the pouch 204 and insert 203 are sized for user.

FIG. 2 is back view of a shirt 201 short sleeve (long sleeve optional). Showing pouch 204 and securable flap 206 for installing and removing insert 203. As shown, the pouch 204 is coupled to the rear portion shirt 201 via a first point of attachment 250 and a second point of attachment 260. The first and second points of attachment 250, 260 coupling the pouch 204 along first and second lengths of the shirt 201. The second point of attachment 260 is oriented parallel to the first point of attachment 250. Also shown, the shirt 201 includes an elastic strap 210 mechanism that extends from the front of the shirt and around the back. It is further shown that the elastic strap 210 extends through a width of the pouch 204. It is further contemplated that the elastic strap 210 may be disposed in the interior of the shirt, or otherwise incorporated as part of the upper body garment, as illustrated by the dotted lines.

FIG. 3 is the front view of shirt 201 shown with fasteners 208 for securing shirt 201 to enable and ease the putting on and taking off of shirt 201. As shown, the elastic strap 210 is coupled to opposing sides of the neck 310, extending under the sleeves or arms and around to the back. It is further contemplated that the elastic strap 210 may be disposed in the interior of the shirt, or otherwise incorporated as part of the upper body garment, as illustrated by the dotted lines.

FIG. 4 is the circular insert 203 which are made from many products including foam and air bladder and are a variety of shapes and sizes depending on user. FIG. 5 is a cross section top view looking down at pouch 204 and insert 203 without flap 206. With (partial) less than ½ circumference mounting indents at rear of shirt 201 with pouch 204 and insert 203 which results in the indenting and self centering of the pouch 204 and insert 203 on the spine of the user 224. Also shirt 201 is short or long sleeve which with pouch 204 and sleeves self centers. Also top of pouch 204 with insert 203 is at shoulder height thereby influencing head to tilt slightly upward and mouth to close slightly while asleep. The pouch 204 and insert 203 are sized for user.

FIG. 6 is the back view of the vest 202 showing circular mounted self centering pouch 204 and securable flap 206 for installing and removing insert 203.

Figure 7:
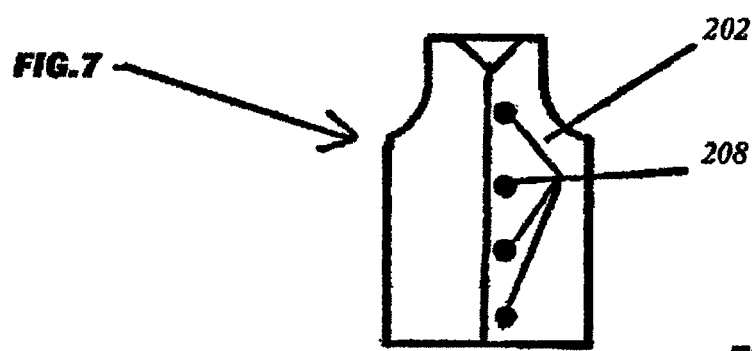
FIG. 7 Is the front view of the vest (shown with fasteners).

FIG. 7 is the front view of the vest 202 with fasteners 208 for securing vest 202 to enable and ease the putting on and taking off of vest 202.

Figure 8:
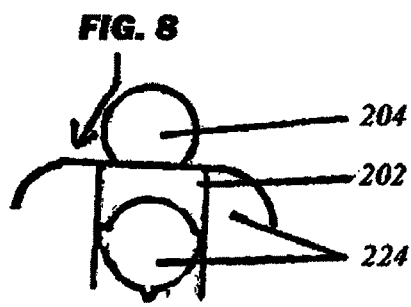
FIG. 8 Is the top back view of vest and pouch and without the insert or flap sized for user extending out from back of vest and will indent in spinal area when insert is in due to partial (less than ½ of) circumference mounting.

FIG. 8 is cross section view looking down from the top at the pouch 204 to show the rear of the vest 202 without the insert 203 or flap 206. The circumference mounting indents into vest 202 and spinal area of user 224 (when insert 203 is in pouch 204). The size of the pouch 204 and insert 203 are sized for the user.

Figure 9:
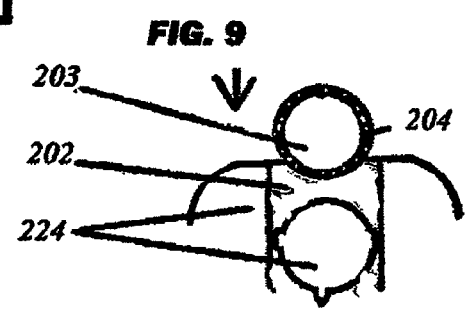
FIG. 9 Is the top back view of vest and pouch without flap showing the indenting (less than ½ of) circumference mounted circular insert (sized and may be other shape depending on need of user) foam, airbladder or other material.

FIG. 9 is a cross section view looking down at pouch 204 and insert 203 without flap 206. With (partial) less than ½ of circumference mounting indenting vest 202 at rear of vest 202 with insert 203 in place which results in self centering and indenting of the insert 203 on the spine. Also top of Pouch 204 and insert 203 are at shoulder height to influence head to tilt slightly upward and mouth to close slightly while asleep. The pouch 204 and insert 203 are sized for user.

Figure 10:
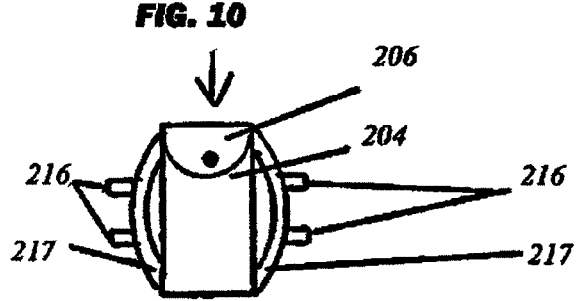
FIG. 10 Is the back of the pouch with securable flap sized for user with partial circumference mounted adjustable straps with fasteners for attachment around upper body and shoulders.

FIG. 10 is the back view of pouch 204 showing securable flap 206 (for installing and removing insert 203) and body adjustable straps 216 and also adjustable shoulder straps 217. These straps 217 and 216 wrap around body 224 and shoulder area and fasten in front of body of user 224. The pouch 204 and insert 203 are sized for user.

Figure 11:
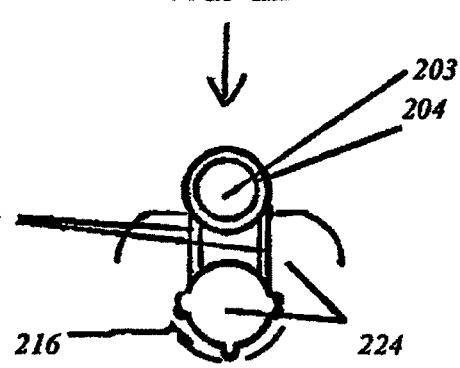
FIG. 11 Is the top view of the pouch and insert without flap sized for user with adjustable straps partial circumference mounted to keep pouch indented and centered in spinal area and is at shoulder blade height or below with fasteners for attachment.

FIG. 11 is the top view of pouch 204 with insert 203 without flap 206. It also shows the body adjustable straps 216 and adjustable shoulder straps 217. It shows the attachment of straps 217 and 216 with partial (less than ½ of) circumference mounted to pouch 204 from back of user which presses pouch 204 in spinal cavity enabling pouch 204 to self center on the spine. Also top of pouch 204 and insert 203 are placed at shoulder height to influence head to tilt slightly upward and the mouth to close slightly while asleep. The pouch 204 and insert 203 are sized for user.

Figure 12:
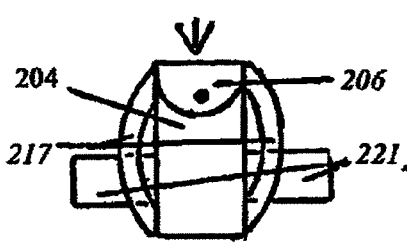
FIG. 12 Is the back of the pouch with securable flap sized for user with a circumference mounted upper body adjustable girdle or brace type wrap and adjustable shoulder straps.

FIG. 12 is the back view of pouch 204 showing girdle type—brace—upper body wrap 221. It also shows pouch 204 with flap 206 (for installing and removing insert 203) and adjustable shoulder straps 217. The wrap 221 and shoulder straps 217 secures at front of body of user. The pouch 204 and insert 203 are sized for user.

Figure 13:
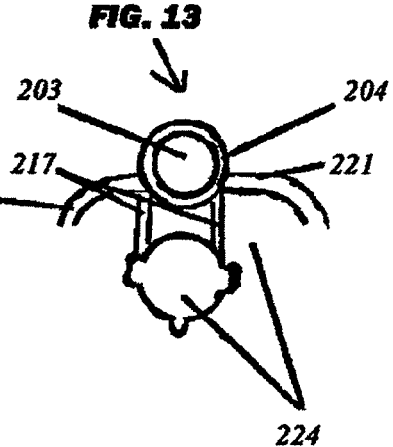
FIG. 13 Is the top back view of pouch without flap and with insert sized for user with partial circumference mounted to upper body girdle or brace and adjustable shoulder straps to keep pouch indented and centered on the spine at shoulder blade height or below with fasteners for attachment.

FIG. 13 is the top view of pouch 204 with insert 203 without flap 206. It also shows the pouch 204 partial(less than ½ of) circumference mounted to the wrap 221 from back of user and presses pouch 204 in spinal cavity causing pouch 204 to indent and self center on spine. Also top of pouch 204 and insert 203 are placed at shoulder height to influence head to tilt upward slightly and the mouth to close slightly while asleep. The pouch 204 and insert 203 are sized for user.

Figure 14:
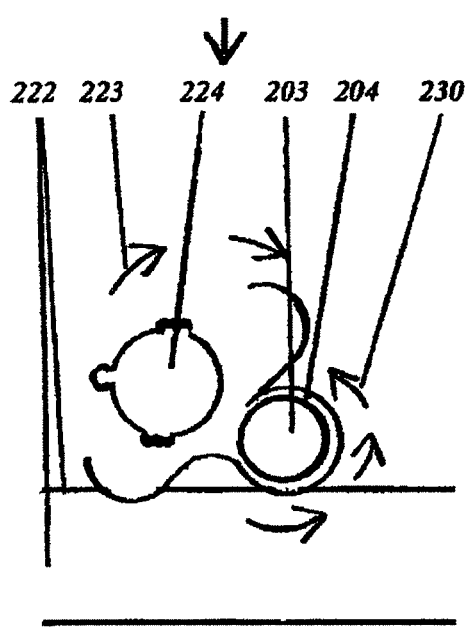
FIG. 14 Is the sleeping view of the pouch and insert without flap with partial circumference mounting when sleeper rolls back against it. It prevents supine position from occurring.

FIG. 14 is a view of user 224 lying on the bed 222 and attempting to achieve a supine direction movement 223. The pouch 204 and insert 203 (sized to user) due to partial (less than ½ of) circumference mounting rotates in opposite direction 230 to create a comfortable movement and achieve about a 60 degree angle to bed 222 (which will also reduce symptoms of position dependent apnea and snoring). This position and the ability to move produces the effect that user 224 will ultimately usually achieve FIG. 15 position (90 degrees) during deep relaxed sleep. This is the position that in most cases minimizes positional dependent apneas and loud snoring.

Figure 15:
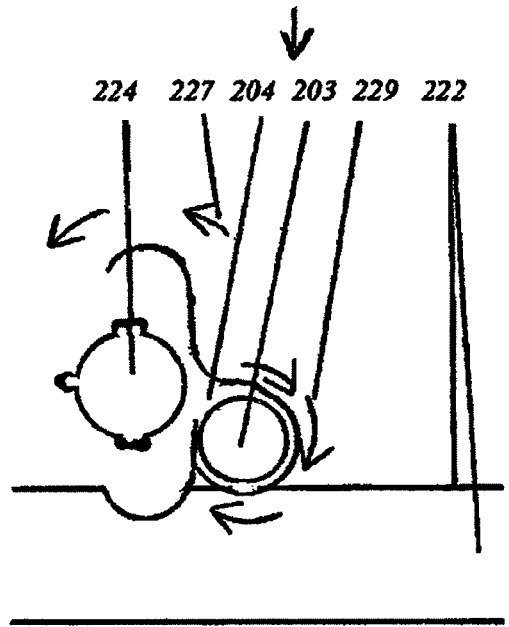
FIG. 15 Is the sleeping view of the pouch and insert without flap with partial circumference mounting when sleeper moves to side position. This position is maintained by many in deep sleep.

FIG. 15 is a view of user 224 lying on the bed 222 and moving to a side position by rotating in direction 227. When user 224 begins to go from position in FIG. 14 to achieve a side sleeping position the pouch 204 with insert 203 (sized to user) due to (partial) less than ½ of circumference mounting rotates in the direction 229 and achieves a position between bed and lower shoulder which in deep sleep (all muscle and reflexes are in hibernation and body is total relaxed) maintains user 224 in side position. Upon beginning to have movement (even when asleep) the user 224 attempts to move and easily overcomes pouch 204 and insert 203 and user 224 has relatively soft comfortable easy movement between positions of FIG. 14 and FIG. 15. These movements occur for various users 224 at varying times depending on user 224 while asleep and going between different stages of sleep. Since the user is about at 60 degrees or greater the user will in most cases assume the side position FIG. 15 during the deep stages of sleep. Many sleep related problems usually are much more severe during these deep stages. Because of total relaxation of muscles in deep sleep position 14 will give moderate benefit but the position 15 gives the maximum benefit to position dependent patients.

The invention claimed is:

1. An upper body garment having a neck opening, two sleeves, and a back, the upper body garment configured to discourage a condition selected from the group consisting of supine sleep, snoring, and positional dependent sleep apnea, the upper body garment comprising:
   an elastic strap coupled to opposing sides of the neck opening, extending under the sleeves and around the back;
   a circular pouch coupled to the back of the upper garment, the circular pouch including:
      a first vertical length of attachment coupling the circular pouch along a first length disposed on the back of the upper garment; and
      a second vertical length of attachment separated from and parallel with the first attachment and coupling the circular pouch along a second length disposed on the back of the upper garment; and
   a substantially cylindrical cushion insert position within the circular pouch.

2. The upper body garment of claim 1, wherein a top portion of the circular pouch is disposed at shoulder height, configured to influence a user's head to tilt upward slightly.

3. The upper body garment of claim 1, wherein the upper body garment is washable.

4. The upper body garment of claim 3, wherein the elastic strap is disposed in the interior of the upper body garment.

5. An upper body garment having a neck opening, two sleeves, and a back, the upper body garment configured to discourage a condition selected from the group consisting of supine sleep, snoring, and positional dependent sleep apnea, the upper body garment comprising:
  an elastic strap coupled to opposing sides of the neck opening, extending under the sleeves and around the back; and
  a circular pouch coupled to the back of the upper garment, the circular pouch including:
    a first point of attachment, the first point of attachment coupling the circular pouch along a first length disposed on the back of the upper garment; and
    a second separated point of attachment, the second point of attachment coupling the circular pouch along a second length disposed on the back of the upper garment, and the second point of attachment oriented substantially parallel to the first point of attachment; and
  a substantially cylindrical insert;
  wherein the coupling of the circular pouch at the first point of attachment and the second point of attachment results in the circular pouch being defined by a discontinuous circle; and
  wherein the circular pouch is sized to receive the substantially cylindrical insert.

6. The upper body garment of claim 5, wherein a top portion of the circular pouch is disposed at shoulder height.

7. The upper body garment of claim 5, wherein the upper body garment is washable.

8. The upper body garment of claim 5, wherein the elastic strap is disposed in the interior of the upper body garment.

* * * * *